(12) United States Patent
Mori et al.

(10) Patent No.: US 6,562,853 B2
(45) Date of Patent: May 13, 2003

(54) 2,5-DIOXO-3-(2-PROPYNYL)IMIDAZOLIDIN-1-YLMETHYL 2,2-DIMETHYL-3-(ALENYL) CYCLOPROPANE CARBOXYLATE COMPOUNDS AND PESTICIDAL METHODS AND COMPOSITIONS UTILIZING THE SAME

(75) Inventors: Tatsuya Mori, Toyonaka (JP); Tomonori Iwasaki, Sanda (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 10/077,901

(22) Filed: Feb. 20, 2002

(65) Prior Publication Data

US 2002/0169329 A1 Nov. 14, 2002

(30) Foreign Application Priority Data

Feb. 22, 2001 (JP) ........................................ 2001-046386

(51) Int. Cl.$^7$ ................... A01N 43/50; C07D 233/72
(52) U.S. Cl. ..................... 514/389; 548/319.5
(58) Field of Search ...................... 548/319.5; 514/389

(56) References Cited

U.S. PATENT DOCUMENTS 4,176,189 A    11/1979   Itaya et al. .................. 424/273

*Primary Examiner*—Laura L. Stockton
(74) *Attorney, Agent, or Firm*—Birch, Stewart, Kolasch & Birch, LLP

(57) ABSTRACT

The present invention provides ester compounds, methods of controlling a pest and uses of the ester compounds. The ester compounds are encompassed by formula (1):

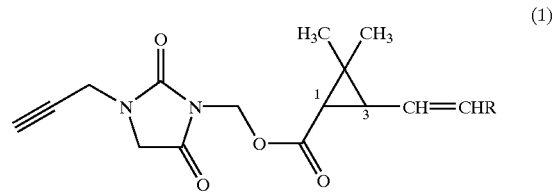

(1)

wherein R represents a C1 to C3 alkyl group. The methods of controlling a pest entail applying the ester compound encompassed by formula (1) to a pest or to a habitat of the pest or both. The uses of the ester compounds encompassed by formula (1) are for controlling pests.

7 Claims, No Drawings

US 6,562,853 B2

2,5-DIOXO-3-(2-PROPYNYL)IMIDAZOLIDIN-1-YLMETHYL 2,2-DIMETHYL-3-(ALENYL) CYCLOPROPANE CARBOXYLATE COMPOUNDS AND PESTICIDAL METHODS AND COMPOSITIONS UTILIZING THE SAME

TECHNICAL FIELD OF THE INVENTION

The present invention relates to ester compounds, methods of controlling a pest and uses of the ester compounds for controlling a pest.

BACKGROUND ART

U.S. Pat. No. 4,176,189 describes utilizing as an active ingredient of an acaricidal composition, certain compounds such as the compound encompassed by formula (A):

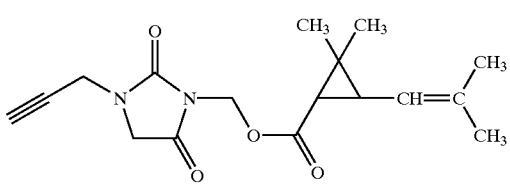

SUMMARY OF THE INVENTION

The present invention provides ester compounds, methods of controlling a pest and uses of the ester compounds. The ester compounds are encompassed by formula (1):

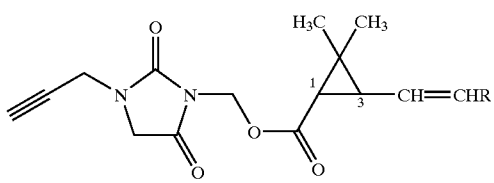

wherein, R represents a C1 to C3 alkyl group. The methods of controlling a pest comprise applying a pesticidally effective amount of an ester compound encompassed by formula (1) to at least one location selected from the pest and a habitat of the pest.

DETAILED DESCRIPTION OF THE INVENTION

The ester compounds encompassed by formula (1) can be designated as 2,5-dioxo-3-(2-propynyl)imidazolidin-1-ylmethyl 2,2-dimethyl-3-(alkenyl)cyclopropanecarboxylate compounds. In the present invention, there can be mentioned as the C1 to C3 alkyl group in formula (1), a methyl group, an ethyl group, a propyl group and an isopropyl group.

The ester compounds encompassed by formula (1) include various pesticidal isomeric forms thereof such as an optical isomer or a geometrical isomer form thereof. Examples of such isomers of the ester compounds encompassed by formula (1) include an optical isomer based on 2 asymmetric carbon atoms present in the cyclopropane ring moiety (R,S), a geometrical isomer based on the C=C double bond therein (E,Z) and the like. Further, the ester compounds encompassed by formula (1) include isomers that are both optical isomers and geometric isomers.

Examples of such isomers of the ester compounds encompassed by formula (1) include the ester compounds wherein in formula (1) the absolute configuration at the 1 position of the cyclopropane ring moiety is a R configuration; the ester compounds wherein in formula (1) the relative configuration of the substituent at the 1 position of the cyclopropane ring moiety with the substituent at the 3 position of the cyclopropane ring moiety is a trans configuration; the ester compounds wherein in formula (1) the relative configuration of the substituent at the 1 position of the cyclopropane ring moiety with the substituent at the 3 position of the cyclopropane ring moiety is a cis configuration; the ester compounds wherein in formula (1) the relative configuration of the C=C double bond at the 3 position of the cyclopropane ring moiety is a Z configuration; the ester compound wherein in formula (1) the absolute configuration at the 1 position of the cyclopropane ring moiety is a R configuration and the relative configuration of the substituent at the 1 position of the cyclopropane ring moiety with the substituent at the 3 position of the cyclopropane ring moiety is a trans configuration; the ester compounds wherein in formula (1) the absolute configuration at the 1 position of the cyclopropane ring moiety is a R configuration and the relative configuration of the substituent at the 1 position of the cyclopropane ring moiety with the substituent at the 3 position of the cyclopropane ring moiety is a cis configuration; the ester compounds wherein in formula (1) the absolute configuration at the 1 position of the cyclopropane ring moiety is a R configuration, the relative configuration of the substituent at the 1 position of the cyclopropane ring moiety with the substituent at the 3 position of the cyclopropane ring moiety is a trans configuration and the relative configuration of the C=C double bond at the 3 position of the cyclopropane ring moiety is a Z configuration; and the ester compounds wherein in formula (1) the absolute configuration at the 1 position of the cyclopropane ring moiety is a R configuration, the relative configuration of the substituent at the 1 position of the cyclopropane ring moiety with the substituent at the 3 position of the cyclopropane ring moiety is a cis configuration and the relative configuration of the C=C double bond at the 3 position of the cyclopropane ring moiety is a Z configuration.

When controlling pests, it is preferred that there is utilized the ester compounds wherein in formula (1) the absolute configuration of the 1 position of the cyclopropane ring moiety is a R configuration. Alternatively, when controlling pests, it is preferred that there is utilized the ester compounds wherein in formula (1) R is a methyl group or ethyl group.

When utilizing a mixture of the isomers of the ester compounds to control pests, the mixture of he isomers thereof may contain at least 70% by moles, and preferably at least 80% by moles, of the ester compounds wherein in formula (1) the relative configuration of the C=C double bond at the 3 position of the cyclopropane ring is a Z configuration. Further, when controlling pests with a mixture of isomers of the ester compounds, it is preferred that the isomer mixture is abundant in the ester compound wherein in formula (1) the absolute configuration of the 1 position of the cyclopropane ring moiety is a R configuration.

The ester compound encompassed by formula (1) can be produced, for example, by the following production methods.

Production Method 1

Production method 1 is a method which has an alcohol compound encompassed by formula (2):

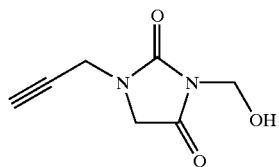

react with at least one of the carboxylic acid compounds encompassed by formula (3):

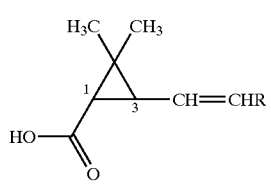

wherein R represents a C1–C3 alkyl group.

The reaction can be carried out by mixing together the alcohol compound encompassed by formula (2) with at least one of the carboxylic acid compounds encompassed by formula (3) in the presence of a condensing agent or acid catalyst, and usually in a solvent.

As examples of the condensing agent utilized in the reaction, there is mentioned dicyclohexylcarbodiimide, 1-ethyl-3-(3-dimethylaminopropyl)carbodiimide hydrochloride and the like. As the examples of the acid catalyst utilized in the reaction, there is mentioned inorganic acids such as sulfuric acid, organic acids such as paratoluene sulfonic acid and methane sulfonic acid and the like.

The solvent utilized in the reaction, is not particularly limited if inert in the reaction. As examples of such solvents, there is mentioned hydrocarbons such as toluene and hexane; ethers such as diethyl ether and tetrahydrofuran; halogenated hydrocarbons such as dichloromethane and 1,2 dichloroethane and the like and solvent mixtures thereof.

The reaction time for such a reaction is usually within a range of from immediately to 72 hours.

The reaction temperature for such a reaction is usually within a range of from −20° C. to 100° C. When utilizing the solvent, it is preferable to have the reaction temperature below the boiling point of the utilized solvent, particularly when the boiling point of the utilized solvent in the reaction is below 100° C.

The reaction may employ a molar ratio wherein, 1 mole of the alcohol compound encompassed by formula (2) maybe utilized for every 1 mole of said at least one of the carboxylic acid compounds encompassed by formula (3). However, it should be noted that the reaction may employ a molar ratio wherein 0.5 to 1.5 moles of the alcohol compound encompassed by formula (2) is utilized for every 1 mole of said at least one of the carboxylic acid compounds encompassed by formula (3).

In carrying out said reaction in the presence of the condensing agent, the amount of the condensing agent utilized in the reaction may change with the conditions of the reaction. Under typical conditions, the reaction usually employs a molar ratio wherein 1 mole of the condensing agent for every 1 mole of said at least one of the carboxylic acid compounds encompassed by formula (3).

Alternatively, when conducting said reaction in the presence of the acid catalyst, a catalytic amount of the acid catalyst be utilized in the reaction.

After the reaction, typical work-up procedures may be conducted with the reaction mixture, such as work-up procedures including pouring the reaction mixture into water, extracting the resulting reaction mixture with an organic solvent and then concentrating the organic layer extracted therefrom. In addition to the work-up procedures, there may be conducted purification methods such as chromotagraphy, if so desired.

Production Method 2

Production method 2 is a method which has the alcohol compound encompassed by formula (2) reacts with a reactive derivative of the carboxylic acid compounds encompassed by formula (3).

As examples of the reactive derivatives of the carboxylic acid compounds encompassed by formula (3), there is mentioned acid halides thereof and acid anhydrides thereof and the like.

Said reaction is typically carried out by mixing together in a solvent in the presence of a base, the alcohol compound encompassed by formula (2) with the reactive derivative of the carboxylic acid compounds encompassed by formula (3).

As examples of the bases utilized in the reaction, there is mentioned organic bases such as trimethylamine, pyridine, N,N-diethylaniline, 4-dimethylaminopyridine and diisopropylethylamine and the like.

The solvents utilized in the reaction, are not particularly limited if inert in the reaction. As examples of such solvents, there is mentioned hydrocarbons such as toluene and hexane; ethers such as diethylether and tetrahydrofuran; halogenated hydrocarbons such as dichloromethane and 1,2-dichloromethane; and the like and mixtures thereof.

The reaction time for such a reaction is usually within a range of from immediately to 72 hours.

The reaction temperature for such a reaction is usually within a range of from −20° C. to 100° C. When utilizing a solvent, it is preferable to have the reaction temperature below the boiling point of the utilized solvent, particularly when the boiling point of the utilized solvent in the reaction is below 100° C.

The reaction may employ a molar ratio in which 1 mole of the alcohol compound encompassed by formula (2) may be utilized for every 1 mole of the reactive derivative of the carboxylic acid compounds encompassed by formula (3). However, the amount of the alcohol compound utilized in the reaction may change, depending on the conditions of the reaction.

In carrying out said reaction in the presence of the base, the amount of the base utilized in the reaction may change with the conditions of the reaction. Under typical conditions, the reaction usually employs a molar ratio wherein 1 mole of the base is utilized for every 1 mole of said at least one of the carboxylic acid compounds encompassed by formula (3).

After the reaction, typical work-up procedures may be conducted with the reaction mixture, such as work-up procedures including pouring the reaction mixture into water, extracting the resulting reaction mixture with an organic solvent and then concentrating the organic layer extracted therefrom. In addition to the work-up procedures, there maybe conducted purification methods such as chromotagraphy, if so desired.

The alcohol compound encompassed by formula (2) can be produced, for example, by the method described in Japanese unexamined patent application U.S. Pat. No. 5,350,859.

The carboxylic acid compounds encompassed by formula (3) can be produced, for example, according to the following scheme 1 and scheme 2.

(scheme 1)

Scheme 1 is expressed as follows:

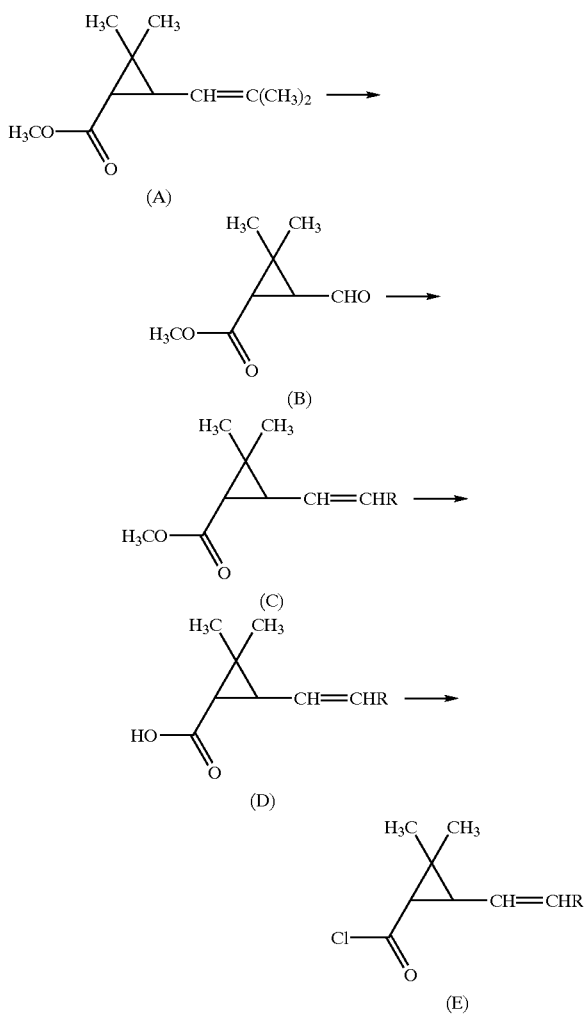

The Method of Producing Compound (B) in Scheme 1

Compound (B) can be produced by subjecting compound (A) to ozone oxidation.

The ozone oxidation of compound (A) can be carried out by adding compound A to a solvent (such as methanol) and blowing ozone into the solvent, followed by adding to the solvent a reducing agent such as dimethyl sulfide.

The reaction temperature of ozone oxidation is typically −100 to −50° C. while blowing ozone into the solvent and is −100 to 50° C. after adding the reducing agent to the solvent.

The reaction time of said reaction is typically from immediately to 72 hours.

After the reaction, the reaction mixture may be concentrated and may be subjected to chromatography to purify compound (B).

The Method of Producing Compound (C) in Scheme 1

Compound (C) can be produced by reacting compound (B) with a phosphorane compound that corresponds with compound (B).

Said reaction is typically carried out by mixing in a solvent compound (B) with the phosphorane compound that corresponds with compound (B). As examples of the solvent, there is mentioned ethers such as tetrahydrofuran and diethyl ester; hydrocarbons such as toluene and the like.

The reaction temperature of said reaction is typically −10 to 50° C.

After the reaction, typical work-up procedures may be conducted with the reaction mixture, such as organic solvent extraction, condensation, concentration and the like. If so desired compound (C) can be purified by purification methods such as chromatography.

The reaction time of said reaction is typically from immediately to 72 hours.

The phosphorane compound utilized in said reaction can by produced by reacting a corresponding phosphonium salt compound with a base. As examples of corresponding phosphonium salt compounds which can be utilized to produce the phosphorane compound in scheme 1, there is mentioned ethyltriphenylphosphonium bromide, propyltriphenylphosphonium bromide and the like. As examples of the base, there is mentioned sodium methoxide, sodium hydride, potassium-t-butoxide and the like.

The Method of Producing Compound (D) in Scheme 1

Compound (D) can be produced by subjecting compound (C) to a hydrolysis reaction. Said hydrolysis reaction is typically carried out by having compound (C) react in the presence of water and in the presence of a base such as sodium hydroxide. The reaction temperature of said hydrolysis reaction is typically 0 to 100° C. After the reaction, reaction mixture may be neutralized and extracted with an organic solvent. The extracted organic layer therefrom may be condensed and concentrated to obtain compound (D). The reaction time of said hydrolysis reaction is typically from immediately to 72 hours.

The Method of Producing Compound (E) in Scheme 1

Compound (E) can be produced by reacting compound (D) with thionyl chloride. Said reaction is typically carried out by mixing together compound (D) and thionyl chloride. Said reaction may be carried out in the presence of or not in the presence of a solvent.

The reaction temperature of said reaction is typically 20 to 100° C.

Further, the reaction may also have present therein a catalytic amount of a nitrogen atom containing compound such as pyridine, N,N-dimethylaminopyridine, N,N-dimethylformamide and the like.

After the reaction, the reaction mixture may be concentrated.

The reaction time of said reaction is typically from immediately to 72 hours.

(scheme 2)

Scheme 2 is a method of producing compound (H), in which the relative configuration of the substituent at the 1 position with the substituent at the 3 position of the cyclopropane ring moiety is in a cis configuration.

Scheme 2 is expressed as follows:

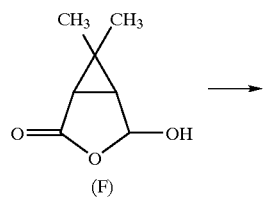

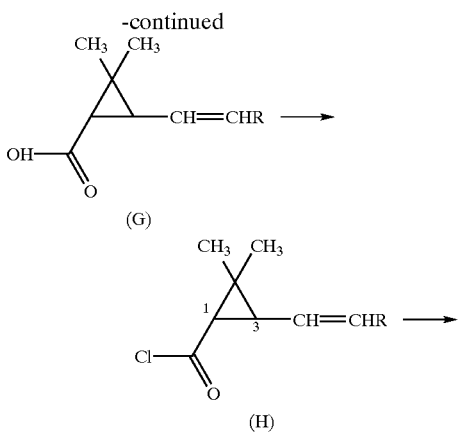

(G)

(H)

The Method of Producing Compound (G) in Scheme 2

Compound (G) can be produced by reacting compound (F) with a phosphorane compound corresponding with compound (F).

Said reaction is typically carried out by mixing in a solvent, compound (F) with said phosphorane compound corresponding with compound (F).

As examples of the solvent, there is mentioned ethers such as diethyl ether; hydrocarbons such toluene and the like.

The reaction temperature of said reaction is typically from −10 to 50° C.

The reaction time of said reaction is typically from immediately to 72 hours.

After the reaction, typical work-up procedures may be conducted with the reaction mixture, such as organic solvent extraction, concentration and the like. If so desired, compound (G) can be purified by purification methods such as chromatography.

The phosphorane compound utilized in said reaction can be produced by reacting a corresponding phosphonium salt compound with a base. As examples of corresponding phosphonium salt compounds that can be utilized to produce the posphorane compound in scheme 2, there is mentioned ethyltriphenylphosphonium bromide, propyltriphenylphosphonium bromide and the like. As bases which can be utilized to produce the phosphorane compound, there is mentioned sodium methoxide, sodium hydride, potassium-t-butoxide and the like.

The Method of Producing Compound (H) in Scheme 2

Compound (H) can be produce similarly to "the method of producing compound (E) in scheme 1", which is described above.

As the pests which can be controlled by the ester compound encompassed by formula (1), there is mentioned Lepidoptera pests, Diptera pests, Dictyoptera pests, Hymenoptera pests, Siphonaptera pests, lice (Anoplura) pests, termites (Isoptera) pests, Hemiptera pests, beetles (Coleoptera) pests, thrips (Thysanoptera) pests, Orthoptera pests, Acarina pests and the like.

Examples of the Lepidoptera pests include Pyralidae such as rice stem borer (*Chiklo suppressalis*), rice leaf roller (*Cnaphalocrocis medinalis*) and Indian meal moth (*Plodia interpunctella*); Noctuidae such as tobacco cutworm (*Spodoptera litura*), rice armyworm (*Pseudaletia separata*) and cabbage armyworm (*Mamestra brassicae*); sulfur butterflies (Pieridae) such as common cabbageworm (*Pieris rapae crucivora*); tortricids (Tortricidae) such as Adoxophyes spp.; Carposinidae; Lyonetiidae; tussock moths (Lymantriidae); Plusiinae; Agrotis spp. such as turnip cutworm (*Agrotis segetum*) and black cutworm (*Agrotis ipsilon*); Helicoverpa spp.; Heliotis spp.; diamondback moth (*Plutella xylostella*); rice skipper (*Parnara guttata*); case-making clothes moth (*Tinea translucens*); webbing clothes moth (*Tineola bisselliella*); and the like.

Examples of the Diptera pests include Culex spp. such as common mosquito (*Culex pipiens pallens*) and *Culex tritaeniorhynchus*; Aedes spp. such as yellow fever mosquito (*Aedes aegypti*) and *Aedes albopictus*; midges (Chironomidae); muscid fly (Muscidae) such as housefly (*Musca domestica*), false housefly (*Muscina stabulans*) and little housefly (*Fannia canicularis*); blow flies (Calliphoridae); flesh flies (Sarcophagidae); seedcorn maggots (*Delia platura*); Anthomyiidae such as onion maggot (*Delia antiqua*); fruit flies (Tephritidae); vinegar flies (Drosophilidae); moth flies (Psychodidae); Phoridae; breeze flies (Tabanidae); black flies (Simuliidae); stable flies (Stomoxyidae); biting midges (Ceratopogonidae) and the like.

Examples of the Dictyoptera pests include German cockroach (*Blattella germanica*); smokybrown cockroach (*Periplaneta fuliginosa*); American cockroach (*Periplaneta americana*); brown cockroach (*Periplaneta brunnea*); oriental cockroach (*Blatta orientalis*); and the like.

Examples of the Hymenoptera posts include ants (Formicidae); hornets (Vespidae); Bethylid wasp (Bethylidae); sawflies (Tentredinidae) such as cabbage sawfly (*Athalis rosae ruficornis*); and the like.

Examples of the Siphonaptera pests include dog flea (*Ctenocephalides canis*); cat flea (*Ctenocephalides felis*); human flea (*Pulex irritans*); and the like Examples of the lice (Anoplura) pests include Pediculidae; crab louse (*Pthirus pubis*); *Pediculus humanus, Pediculus corporis*; and the like.

Examples of the termites (Isoptera) pests include *Reticulitermes speratus*; Formosan subterranean termite (*Coptotermes formosanus*); and the like.

Examples of the Hemiptera pests include Delphacidae (planthoppers) such as small brown planthopper (*Laodelphax striatellus*), brown planthopper (*Nilaparvata lugens*) and white backed rice planthopper (*Sogatella furcifere*); leafhoppers (Deltocephalidae) such as green rice leafhopper (*Nephotettix cincticeps*) and green rice leafhopper (*Nephotettix virescens*); aphids (Aphididae); Heteroptera (plant bugs); whiteflies (Aleyrodidae); scales; lace bugs (Tingidae); jumping plantlice (Psyllidae); and the like.

Examples of the beetles (Coleoptera) pests corn rootworms such as black carpet beetle (Attagenus unicolor japonicus), western corn rootworm (*Diabrotica virgifera*) and southern corn rootworm (*Diabrotica undecimpunctata howardi*); scarabs (Scarabaeidae) such as cupreous chafer (*Anomala cuprea*) and soybean beetle (*Anomala rufocuprea*); weevils (Curculionidae) such as maize weevil (*Sitophilus zeamais*), ricewater weevil (*Lissorhoptrus oryzophilus*), ball weevil and adzuki bean weevil (*Collosobruchus chinensis*); darkling beetles (Tenebrionidae) such as yellow mealworm (*Tenebrio molitor*) and red flour beetle (*Tribolium castaneum*); leaf beetles (Chrysomelidae) such as rice leaf beetle (*Oulema oryzae*), striped flea beetle (*Phyllotreta striolata*) and cucurbit leaf beetle (*Aulacophora femoralis*); deathwatch beetles (Anobiidae); Epilachna spp. such as twenty-eight spotted ladybirds (*Epilachna vigintioctopunctata*); powderpost beetles (Lyctidae); false powderpost beetles (Bostrychidae); longicorn beetles (Cerambycidae); robe beetle (*Paederus fuscipes*); and the like.

Examples of the thrips (Thysanoptera) pests include *Thrips palmi*; western flower thrips (*Flankiniella occidentalis*); flower thrip (*Thrips hawaiiensis*) and the like.

Examples of the Orthoptera pests include mole crickets (Gryllotalpidae); grasshoppers (Acrididae); and the like.

Examples of the Acarina pests include Dermanyssidae such as American house dust mite (*Dermatophagoides farinae*) and *Dermatophagoides pteronyssinus*; acarid mites (Acaridae) such as mold mite (*Tyrophagus putrescentiae*) and brown legged grain mite (*Aleuroglyphus ovatus*); Glycyphagidae such as *Glycyphagus privatus, Glycyphagus domesticus* and groceries mite (*Glycyphagus destructor*); Cheyletidae such as *Chelacaropsis malaccensis* and *Cheyletus fortis*; Tarsonemidae; Chortoglyphus spp.; *Haplochthonius simplex*; Tetranychidae such as two-spotted spider mite (*Tetranychus urticae*), Kanzawa spider mite (*Tetranychus kanzawai*), citrus red mite (*Panonychus citri*) and (European red mite (*Panonychus ulmi*); ticks (Ixodidae) such as *Haemaphysalis longiconis*; and the like.

When utilizing the ester compounds encompassed by formula (1) to control pests, an ester compound encompassed by formula (1) is usually applied to at least one location selected from the pest or a habitat of the pest. In such cases, there may be applied, the ester compound by itself or a pesticidal composition comprising a pesticidally effective amount of at least one of the ester compounds encompassed by formula (1). For example, the pesticidal composition can be applied so that the ester compounds encompassed by formula (1) are applied in an amount of from 1 to 5000 mg, to 1 $m^2$ to 1 $m^3$ of the said at least one location.

As examples of formulations of the ester compounds encompassed by formula (1), there is mentioned oily formulations; emulsifiable concentrates; wettable powders; flowables such as aqueous suspensions and aqueous emulsions; granules; dusts; aerosols; heating volatile formulations such as mosquito-coils, mosquito-mats for electric heaters and liquids for electric heaters; fumigants such as combustible fumigants, chemical fumigants and porous ceramic plate fumigants; non-heating volatile formulations such as resin volatile formulations and paper volatile formulations; fogging formulations; ULV formulations; pesticidal baits; and the like.

The formulations typically contain the ester compounds encompassed by formula (1) in an amount of from 0.001 to 95% by weight. However, the amount of the ester compounds encompassed by formula (1) present in the formulations may change with the type of formulation.

As formulation methods, for example, there is mentioned the following general methods.

(I) formulation methods entailing mixing an ester compound encompassed by formula (1) with a solid carrier, a liquid carrier, a gaseous carrier or a baiting agent. In such cases, there can be optionally utilized therein a surfactant or other formulation auxiliaries.

(II) formulation methods entailing impregnating an ester compound encompassed by formula (1) onto a base material comprising no pesticidally active ingredient.

(III) a formulation method entailing mixing an ester compound encompassed by formula (1) with the base material and molding the resulting mixture into a desired shape.

As examples of the solid carriers utilized when formulating, there is mentioned clays such as kaolin clay, diatomaceous earth, synthetic hydrated silicon oxide, bentonite, Fubasami clay and acid clay; talcs; ceramics; other inorganic minerals such as sericite, quartz, sulfur, active carbon, calcium carbonate, hydrated silica and montmorillonite; chemical fertilizers such as ammonium sulfate, ammonium phosphate, ammonium nitrate, urea and ammonium chloride; and the like.

As examples of the liquid carriers utilized when formulating, there is mentioned water; alcohols such as methanol and ethanol; ketones such as acetone and methyl ethyl ketone; aromatic hydrocarbons such as benzene, toluene, xylene, ethyl benzene, methylnaphthalene and phenylxylylethane; Miphatic hydrocarbons such as hexane, cyclohexane, kerosene and gas oil; esters such as ethyl acetate and butyl acetate; nitriles such as acetonitrile and isobutyronitrile; isobutyronitrile; ethers such as diisopropyl ether and dioxane; acid amides such as N,N-dimethylformamide and N,N-dimethylacetamide; halogenated hydrocarbons such as dichloromethane, trichloroethane and carbon tetrachloride; dimethyl sulfoxide; vegetable oils such as soybean oil and cottonseed oil; and the like.

As examples of gaseous carriers utilized when formulating, there is mentioned freon gas, butane gas, LPG (liquefied petroleum gas), dimethyl ether, carbon dioxide and the like.

As examples of the surfactant utilized when formulating, there is mentioned alkyl sulfates, alkylsulfonates, alkylarylsulfonates, alkyl aryl ethers, polyoxyethylenealkyl aryl ethers, polyethylene glycol ethers, polyhydric alcohol esters, sugar alcohol derivatives and the like.

As examples of the other formulation auxiliaries, there are mentioned adhesives, spreading agents, stabilizers and the like. More specifically, examples of the other formulation auxiliaries include casein; gelatin; polysaccharides such as starch, gum arabic, cellulose derivatives and alginic acid; lignin derivatives; bentonite; sugars; and synthetic water-soluble polymers such as polyvinyl alcohol and polyvinylpyrrolidone; polyacrylic acid; SHT (2,6-di-tert-butyl-4-methyphenol); BHA (mixture of 2-tert-butyl-4-methoxyphenol and 3-tert-butyl-4-methoxyphenol) and the like.

When formulating into mosquito coils, an ester compound encompassed by formula (1) can be mixed with the base material and binding agent and then formed into the desired shape. As the base material, there may be utilized mixtures of raw plant powders such as mixtures of wood powders or of Pyrethrum marcs. Examples of the binding agent include Tabu powders, starches, glutens and the like When formulating into mosquito mats, an ester compound encompassed by formula (1) can be impregnated onto the base material, with examples of such base materials including a plate which has compacted cotton linters, a plate which has compacted a fibril mixture of such as cotton linter with pulp and the like.

As examples of the components when formulating into the combustible fumigants, there is mentioned exothermic agents such as nitrate, zinc nitrate, guanidine salt, potassium chlorate, nitrocellulose, ethylcellulose and wood powder; pyrolytic stimulating agents such as alkali metal salt, alkaline earth metal salt, dichromate and chromate; oxygen sources such as potassium nitrate; combustion assistants such as a melanin and wheat starch; bulk fillers such as diatomaceous earth; binding agents such as synthetic glue; and the like.

As examples of the components when formulating into the chemical fumigants, there is mentioned exothermic agents such as alkali metal sulfide, polysulfide, hydrogensufide, hydrated salt and calcium oxide; catalytic agents such as carbonaneous substance, iron carbide and activated clay; organic foaming agents such as azodicarbonamide, benzenesulfonylhydrazide, dinitropentamethylene tetramine, polystyrene and polyurethane; fillers such as a natural fiber and synthetic fiber; and the like.

As examples of the components when formulating the non-heating volatile formulations, there is mentioned thermoplastic resins, paper such as filter paper and Japanese paper and the like.

As examples of components when formulating the pesticidal bait, there is mentioned bait components such as a grain powder, vegetable oil, sugar and crystalline cellulose; antioxidants such as dibutylhydroxytoluene and nordihydroguaiaretic acid; preservatives such as dihydroacetic acid, substances for preventing ingestion by children or pets such as red pepper powder, attractants such as cheese flavor, onion flavor and peanut oil; and the like.

When utilizing the formulations to control pests, the following are mentioned and can be chosen according to the form of formulation and to the location to which the formulation is utilized.

(A) methods entailing directly applying the formulation to the pest or to the habitat of the pest.

(B) methods entailing diluting the formulation with a solvent such as water and then applying the diluted formulation to the pest or the habitat of the pest.

(C) methods entailing heating the formulation at a habitat of the pest.

When diluting the formulation to control the pest, the formulation is usually diluted so that the ester compounds encompassed by formula (1) are present therein at a concentration of from 0.1 to 10,000 ppm. Examples of formulations that are typically diluted to control the pests include emulsifiable concentrates, wettable powders, flowables or microcapsules and the like.

When heating the formulation to control pests, the application amount and application concentration of the present invention compound is usually pre-determined appropriately before the application, according to the formulation type, application time, application location, application method, type of the pest damage conditions and the like.

If so desired, the pesticidal compositions of the present invention can have optionally added thereto a soil disinfectant, a fungicide, a herbicide, a plant growth regulator, a pest repellant, a synergist, a fertilizer, a soil improving agent, other pesticidally effective agents or the like.

Examples of the other pesticidally effective agents which may be added to the pesticidal compositions include organophosphorus compounds such as fenitrothion (O,O-dimethyl O-(3-methyl-4-nitrophenyl)phosphorothioate), fenthion (O,O-dimethyl O-(3-methyl-4-(methythio)phenyl) phosphorothioate), diazinon (O,O-diethyl O-2-isopropyl-6-methylpyrimidin-4-yl phosphorothioate), chlorpyrifos (O,O-diethyl O-3,5,6-trichloro-2-pyridyl phosphorothioate), acephate (O,S-dimethyl acetylphosphoramidothioate), methidathion (S-2,3-dihydro-5-methoxy-2-oxo-1,3,4-thiadiazol-3-ylmethyl O,O-dimethyl phosphorodithioate), disulfoton (O,O-diethyl S-2-ethylthioethyl phosphorodithioate), DDVP (2,2-dichlorovinyl dimethyl phosphate), sulprofos (O-ethyl O-4-(methylthio)phenyl S-propyl phosphorodithioate), cyanophos (O-4-cyanophenyl O,O-dimethyl phosphorothioate), dioxabenzofos (2-methoxy-4H-1,3,2-benzodioxaphosphinine-2-sulfide), dimethoate (O,O-dimethyl S-(N-methylcarbamoylmethyl) dithiophosphate), phenthoate (ethyl 2-dimethoxyphosphinothioylthio(phenyl) acetate), malathion (diethyl (dimethoxyphosphinothioylthio) succinate), trichlorfon (dimethyl 2,2,2-trichloro-1-hydroxyethylphosphonate), azinphos-methyl (S-3,4-dihydro-4-oxo-1,2,3-benzotriazin-3-ylmethyl O,O-dimethyl phosphorodithioate), monocrotophos (dimethyl (E)-1-methyl-2-(methylcarbamoyl)vinyl phosphate) and ethion (O,O,O',O'-tetraethyl S,S'-methylene bis (phosphorodithioate);

carbamate compounds such as BPMC (2-sec-butylphenyl methylcarbamate), benfracarb (ethyl N-[2,3-dihydro-2, 2-dimethylbenzofuran-7-yloxycarbonyl(methyl) aminothio]-N-isopropyl-β-alaninate), propoxur (2-isopropoxyphenyl N-methylcarbamate), carbosulfan (2,3-dihydro-2,2-dimethyl-7-benzo[b]furanyl N-dibutylaminothio-N-methylcarbamate), carbaryl (1-naphthyl N-methylcarbamate), methomyl (S-methyl N-[(methylcarbamoyl)oxy]thioacetimidate), ethiofencarb (2-(ethylthiomethyl)phenyl methylcarbamate), aldicarb (2-methyl-2-(methylthio) propionaldehyde O-methylcarbamoyloxime), oxamyl (N,N-dimethyl-2-methylcarbamoyloxyimino-2-(methylthio)acetamide) and fenothiocarb (S-4-phenoxybuthyl N,N-dimethylthiocarbamate);

pyrethroid compounds such as etofenprox (2-(4-ethoxyphenyl)-2-methylpropyl 3-phenoxybenzyl ether), fenvalerate ((RS)-α-cyano-3-phenoxybenzyl (RS)-2-(4-chlorophenyl)-3-methylbutyrate), esfenvalerate ((S)-α-cyan-3-phenoxybenzyl (S)-2-(4-chlorophenyl)-3-methylbutyrate), fenpropathrin ((RS)-α-cyano-3-phenoxybenzyl 2,2,3,3-tetramethylcyclopropane-carboxylate), cypermethrin ((RS)-α-cyano-3-phenoxybenzyl (1RS)-cis,trans-3-(2,2-dichlorovinyl)-2,2-dimethyl-cyclopropanecarboxylate), permethrin (3-phenoxybenzyl (1RS)-cis,trans-3-(2,2-dichlorovinyl)-2,2-dimethylcyclopropane-carboxylate), cyhalothrin ((RS)-α-cyano-3-phenoxybenzyl (Z)-(1RS)-cis-3-(2-chloro-3,3,3-trifluoroprop-1-enyl)-2,2-dimethylcyclopropanecarbo xylate), deltamethrin ((S)-α-cyano-3-phenoxybenzyl (1R)-cis-3-(2,2-dibromovinyl)-2,2-dimethyl-cyclopropanecarboxylate), cycloprothrin ((RS)-α-cyano-3-phenoxybenzyl (RS)-2,2-dichloro-1-(4-ethoxyphenyl) cyclopropanocarboxylate), fluvalinate (α-cyano-3-phenoxybenzyl N-(2-chloro-α,α, α-trifluoro-p-tolyl)-D-valinate), bifenthrin (2-methylbiphenyl-3-ylmethyl (Z)-(1RS)-cis-3-(2-chloro-3,3,3-trifluoroprop-1-enyl)-2,2-dimethyl-cyclopropanecarbo xylate), halofenprox (2-(4-bromodifluoromethoxyphenyl)-2-methylpropyl 3-phenoxybenzyl ether), tralomethrin ((S)-α-cyano-3-phenoxybenzyl (1R)-cis-3-(1,2,2,2-tetrabromoethyl)-2, 2-dimethylcyclopropane-carboxylate), silafluofen ((4-ethoxyphenyl)(3-(4-fluoro-3-phenoxyphenyl)propyl) dimethylsilane), d-phenothrin (3-phenoxybenzyl (1R)-cis,trans-2,2-dimethyl-3-(2-methyl-1-propenyl) cyclopropanecarboxylate), cyphenothrin ((RS)-α-cyano-3-phenoxybenzyl (1R)-cis,trans-2,2-dimethyl-3-(2-methyl-1-propenyl)cyclopropanecarboxylate), d-resmethrin (5-benzyl-3-furylmethyl (1R)-cis,trans-2, 2-dimethyl-3-(2-methyl-1-propenyl)cyclopropane-carboxylate), acrinathrin ((S)-α-cyano-3-phenoxybenzyl (1R,3Z)-cis-(2,2-dimethyl-3(3-oxo-3-(1,1,1,3,3,3-hexafluoropropyloxy)propenyl)cycl opropanecarboxylate), cyfluthrin ((RS)-α-cyano-4-fluoro-3-phenoxybenzyl 3-(2,2-dichlorovinyl)-2,2-dimethylcyclopropanecarboxylate), tefluthrin (2,3,5,6-tetrafluoro-4-methylbenzyl (1RS,3Z)-cis-3-(2-chloro-3,3,3-trifluoro-1-propenyl)-2,2-dimethylcyclopropanecarbox ylate), transfluthrin (2,3,5,6-tetrafluorobenzyl (1R)-trans-3-(2,2-dichlorovinyl)-2,2-dimethylcyclopropanecarboxylate), tetramethrin (3,4,5,6-tetrahydrophthalimidomethyl (1RS)-cis,trans-2,2-dimethyl-3-(2-methyl-1-propenyl) cyclopropanecarboxylate), allethrin ((RS)-3-alkyl-2- methyl-4-oxocyclopent-2-enyl (1R,3RS; 1RS,3SR)-2,2-dimethyl-3-(2-methylprop-1-enyl)cyclopropanecarboxylate, d-furamethrin (5-(2-propynyl)furfuryl (1R)-cis,trans-2,2-dimethyl-3-(2-methyl-1-propenyl)cyclopropanecarboxylate), prallethrin ((S)-2-methyl-4oxo-3-(2-propyl)cyclopent-2-enyl (1R)-cis,trans-chrysanthmate), empenthrin ((RS)-1-ethynyl-2-methyl-2-pentenyl (1R)-cis,trans-2,2-dimethyl-3-(2-methyl-1-propenyl)cyclopropanecarboxylate) and 5-(2-propynyl)furfuryl 2,2,3,3-tetamethylcyclopropanecarboxylate;

nitroimidazolidine derivatives; N-cyanoamidine derivatives such as N-cyano-N'-methyl-N'-(6-chloro-3-pyridylmethyl)acetamidine; chlorinated hydrocarbons such as endosulfan (6,7,8,9,10,10-hexachloro-1,5,5a,6,9,9a-hexahydro-6,9-methano-2,4,3-benzodioxathiepine 3-oxide), γ-BHC (1,2,3,4,5,6-hexachlorocyclohexane) and dicofol (1,1-bis (chlorophenyl)-2,2,2-trichloroethanol); benzoylphenylurea compounds such as chlorofluazuron (1-(3,5-dichloro-4-(3-chloro-5-trifluoromethylpyridyn-2-yloxy)phenyl)-3-(2,6-difluoro benzoyl)urea), teflubenzuron (1-(3,5-dichloro-2,4-difluorophenyl)-3-(2,6-difluorobenzoyl)urea) and flufenoxuron (1-(4-(2-chloro-4-trifluoromethylphenoxy)-2-fluorophenyl)-3-(2,6-difluorobenzoyl)urea); metoxadiazone (5-methoxy-3-(2-methoxyphenyl)-1,3,4-oxadiazol-2-(3H)-one); bromopropylate (isopropyl 4,4'-dibromobenzilate); tetradifon (4-chlorophenyl 2,4,5-trichlorophenyl sulfone); chinomethionate (S,S-6-methylquinoxaline-2,3-diyldithiocarbonate); pyridaben (2-tert-butyl-5-(4-tert-butylbenzylthio)-4-chloropyridazin-3(2H)-one); fenpyroximate (tert-butyl (E)-4-[(1,3-dimethyl-5-phenoxypyrazol-4-yl)methyleneaminooxymethyl]benzoate); diafenthiuron (N-(2,6-diisopropyl-4-phenoxyphenyl)-N'-tert-butylthiourea); tebufenpyrad (N-(4-tert-butylbenzyl)-4-chloro-3-ethyl-1-methyl-5-pyrazolencarboxamide); polynactins complex (tetranactin, dinactin and trinactin); pyrimidifen (5-chloro-N-[2-(4-(2-ethoxyethyl)-2,3-dimethylphenoxy)ethyl]-6-ethylpyrimidin-4-am ine); milbemectin; abamectin; ivermectin; azadirachtin (AZAD); and the like.

As examples of the pest repellant, there is mentioned 3,4-caranediol, N,N-diethyl-m-toluamide, 1-methylpropyl 2-(2-hydroxyethyl)-1-piperidinecarboxylate, p-menthane-3,8-diol, botanical essential oils such as hyssop oil and the like.

As examples of the synergist, there is mentioned bis-(2,3,3,3-tetrachloropropyl) ether (S-421), N-(2-ethylhexyl) bicyclo [2.2.1]hept-5-ene-2,3-dicarboximide (MGK-264), α-[2-(2-butoxyethoxy)ethoxy]-4,5-methylenedioxy-2-propyltoluene (piperonyl butoxide) and the like.

EXAMPLES

Hereinafter, the present invention is described more specifically by the production examples, formulation examples and the test examples, but the present invention is not limited thereto.

The production examples of the ester compounds encompassed by formula (1) are provided below.

Production Example 1

After 2.1 g of pyridine and 4.0 g of the alcohol compound encompassed by formula (2);

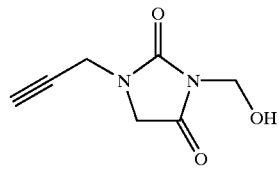

(2)

were dissolved in 65 ml of tetrahydrofuran, 4.1 g of (1R)-trans-2,2-dimethyl-3-(1-propenyl)cyclopropanecarboxylic chloride, which was produced by reference example 1 below, was added thereto under ice cooled conditions. The resulting reaction mixture was stirred at room temperature for 8 hours. Subsequently, the reaction mixture was concentrated to provide a residue. One hundred and fifty milliliters (150 ml) of ethyl acetate were added to the residue. After the mixture was poured into 50 ml of ice water, the resulting mixture was allowed to settle to form an aqueous layer and an organic layer. The organic layer was then extracted from the mixture. The organic layer was washed with saturated brine, was dried with anhydrous magnesium sulfate and was concentrated to provide a second residue. The second residue was subjected to silica gel column chromatography to provide 4.72 g of 2,5-dioxo-3-(2-propynyl)imidazolidin-1-ylmethyl (1R)-trans-2,2-dimethyl-3-((Z)1-propenyl)cyclopropanecarboxylate (present invention compound 1) (65% yield).

$^1$H-NMR (CDCl$_3$, TMS inner standard, δ values (ppm): 1.14(s,3H), 1.28(s,3H, 1.44(d,1H), 1.70(d,3H), 2.28(m,1H), 2.36(t,1H), 4.06(s,2H), 4.27(d,2H), 5.10(m,1H), 5.55(dd, 2H), 5.60(m,1H)

Production Example 2

After 0.52 g of pyridine and 1.0 g of the alcohol compound encompassed by formula (2) were dissolved in 10 ml of tetrahydrofuran, 1.17 g of (1R)-trans-2,2-dimethyl-3-(1-butenyl)-cyclopropanecarboxylic chloride, which was produced by reference example 2 below was added thereto under ice cooled conditions. The resulting reaction mixture was stirred at room temperature for 8 hours. Subsequently, the reaction mixture was poured into 30 ml of ice water and the organic layer was extracted therefrom twice with 50 ml of ethyl acetate. After the organic layers were combined to form one mixture, the mixture was washed with saturated brine, was dried with anhydrous magnesium sulfate and was concentrated under reduce pressure to provide a residue. The residue was subjected to silica gel column chromatography to provide 1.23 g of 2,5-dioxo-3-(2-propynyl)imidazolidin-1-ylmethyl (1R)-trans-2,2-dimethyl-3-((Z)1-butenyl)cyclopropanecarboxylate (present invention compound 2) (65% yield).

$^1$H-NMR (CDCl$_3$, TMS inner standard, δ values (ppm): 0.97(t,3H), 1.12(s,3H), 1.27(s,3H), 1.44(d,1H), 2.14(m,2H+1H), 2.37(t,1H), 4.05(s,2H), 4.27(d,2H), 5.03(m,1H), 5.54(m,2H+1H)

Production Example 3

After 0.44 g of pyridine and 0.84 g of the alcohol compound encompassed by formula (2) were dissolved in 10 ml of tetrahydrofuran, 0.91 g of (1R)-cis-2,2-dimethyl-3-(1-propenyl)cyclopropanecarboxylic chloride was added thereto under ice cooled conditions. The resulting reaction mixture was stirred at room temperature for 8 hours. Subsequently, the reaction mixture was poured into 30 ml of ice water and the organic layer was extracted twice therefrom with 40 ml of ethyl acetate. After the organic layers were combined to form one mixture, the mixture was washed with saturated brine, was dried with anhydrous magnesium sulfate and was then concentrated under reduce pressure to provide a residue. The residue was subjected to silica gel column chromatography to provide 0.98 g of 2,5-dioxo-3-(2-propynyl)imidazolidin-1-ylmethyl (1R)-cis-2,2-dimethyl-3-((Z)1-propenyl)cyclopropanecarboxylate (present invention compound 3) (64% yield).

$^1$H-NMR (CDCl$_3$, TMS inner standard, δ values (ppm): 1.20(s,3H), 1.25(s,3H, 1.70(brd,3H+1H), 2.05(t,1H), 2.42(t, 1H), 4.05(s,2H), 4.27(d,2H), 5.48(dd,2H), 5.65(m,2H)

Reference Example 1

To a mixture containing 430 g of methanol and 265 g of pyridine, under ice cooled conditions, 501.9 g of 3-(2-methyl-1-propenyl)-2,2-dimethylcyclopropanecarboxylic chloride {wherein the molar ratio of the (1R)-trans compound: (1R)-cis compound: (1S)-trans compound: (1S)-cis compound was 93.9:2.5:3.5:0.1} was added over 2.5 hours while stirring the reaction mixture. Subsequently, the reaction mixture was further stirred at room temperature over 4 hours. After concentrating the reaction mixture under reduced pressure to about half of its volume, the reaction mixture was eye-dropped into 500 ml of 3.5% hydrochloric acid. The resulting mixture was extracted 3 times with 200 ml of methyl-t-butyl ether and then concentrated to provide a residue. The resulting residue was distilled under reduced pressure (84 to 89° C./7 mmHg) to provide 426 g of methyl 3-(2-methyl-1-propenyl)-2,2-dimethylcyclopropanecarboxylate.

One hundred and fifty grams (150 g) of methyl 3-(2-methyl-1-propenyl)-2,2-dimethylcyclopropanecarboxylate was dissolved in 1000 ml of methanol. Ozone was then blown into the reaction mixture at −50 to −60° C. After confirming with gas chromatography the consumption of methyl 3-(2-methyl-1-propenyl)-2,2-dimethylcyclopropanecarboxylate, the oxone blowing was stopped and 170 g of dimethylsulfide were eye-dropped into the mixture. The reaction mixture was then left overnight, allowing the reaction mixture to warm to room temperature. The mixture was concentrated under reduced pressure to provide a residue. Five hundred milliliters (500 ml) of methyl-t-butyl ether and 1000 ml of 10% hydrochloric acid was added and stirred into the residue. After allowing the mixture to settle at room temperature for 2 hours, the aqueous layer was extracted therefrom. The aqueous layer was then mixed with 500 ml of methyl-t-butyl ether and 1000 ml of 10% hydrochloric acid. The organic layer was then extracted therefrom, washed with 500 ml of saturated aqueous sodium hydrogencarbonate and concentrated under reduced pressure to provide a residue. The residue was distilled under reduced pressure (84 to 103° C./7 mmHg) to provide 88.9 g of methyl 2,2-dimethyl 3-formylcyclopropanecarboxylate.

Under a nitrogen environment, in a 4-mouth 500 ml flask, 20.3 g of sodium methoxide was suspended in 138.8 g of tetrahydrofuran and cooled to 0° C. Subsequently, 111.5 g of ethyltriphenylphosphoniun bromide were added to the suspension over 5 minutes. After stirring at 0 to 5° C. for 1 hour, 73.3 g of a toluene solution of methyl 2,2-dimethyl-3-formylcyclopropanecarboxylate (purely, 39.1 g of methyl 2,2-dimethyl-3-formylcyclopropanecarboxylate ester) was eye-dropped thereto over 5.5 hours at 0 to 5° C.

After stirring the resulting reaction mixture for 1.5 hours at 0 to 5° C., 42.0 g of 10% hydrochloric acid was added thereto so that the aqueous layer therein was calibrated to have a pH of 6.85.

The reaction mixture then had 198.9 g of water added thereto and was heated to a solution temperature of 74 to 82° C., in order to distill therefrom 130 ml of tetrahydrofuran and toluene.

Further, the resulting residue had 192.8 g of water added thereto and was heated to a solution temperature of 84.6 to 102.1° C. (bath temperature 109 to 131° C.) for a second distillation. During the second distillation, 391 g of water was eye-dropped thereto over 4.5 hours after reaching a solution temperature of 93° C.

After allowing the distillate to settle, there was present therein 411.7 g of the aqueous layer and 73.4 g of the organic layer. The organic layer was extracted therefrom. The organic layer was measured to have 53.7% by weight of methyl 2,2-dimethyl-3-(1-propenyl)cyclopropanecarboxylate (measured with the inner standard method using gas chromatography).

Under reduced pressure 723 g of the organic layer was then concentrated to provide 38.7 g of methyl 2,2-dimethyl-3-(1-propenyl)cyclopropanecarboxylate (yield 91.9%). In the isolated methyl 2,2-dimethyl-3-(1-propenyl) cyclopropanecarboxylate, there was a mixture of isomers in which the molar ratio of methyl 2,2-dimethyl-3-((Z)1-propenyl)cyclopropanecarboxylate to methyl 2,2-dimethyl-3-((Z)1-propenyl)cyclopropanecarboxylate was 1:9.

Subsequently, 491.1 g of methyl 2,2-dimethyl-3-(1-propenyl)cyclopropanecarboxylate were dissolved into 307.5 g of toluene and 98.4 g of methanol. While preserving the resulting solution at 60° C., 526.4 g of a 40% sodium hydroxide solution was stirred into the solution over 1.5 hours. The resulting reaction mixture was further stirred for 1 hour at 60° C.

After cooling the reaction mixture to 30° C., 394.8 g of water was added thereto. After allowing the reaction mixture to settle, the reaction mixture was separated into an organic layer and aqueous layer. The aqueous layer had 1152 g of 20% hydrochloric acid added thereto and was then extracted five times with 451 g toluene. After the organic layers therefrom were combined, the resulting mixture was dried with dehydrated magnesium sulfate and concentrated under reduced pressure to provide 464.7 g of 2,2-dimethyl-3-(1-propenyl)cyclopropanecarboxylic acid.

To a mixture containing 464.7 g of 2,2-dimethyl-3-(1-propenyl)cyclopropanecarboxylic acid, 464.7 g of hexane and 0.17 g of pyridine, 430.2 g of thionyl chloride was eye-dropped thereto at 50° C. over 3 hours. The reaction mixture was further stirred for 1 hour. The reaction mixture was then concentrated under reduced pressure to provide 472.3 g of (1R) trans-2,2-dimethyl-3-(1-propenyl) cyclopropanecarboxylic chloride.

Reference Example 2

A method of producing (1R)trans-2,2-dimethyl-3-(1-butenyl)cyclopropanecarboxylic chloride Under a nitrogen environment, 109 g of n-propyltriphenylphosphonium bromide was suspended in 200 ml of tetrahydrofuran and 31.6 g of potassium-t-butoxide was added thereto over 5 minutes at 0° C. The mixture was then stirred at 0 to 5° C. for 1 hour. To the mixture, there was eye-dropped at 0 to 5° C. over 30 minutes, a solution in which 40.0 g of methyl 2,2-dimethyl-3-formylcyclopropanecarboxylate, as produced in Reference Example 1 above, was dissolved in 40 ml of tetrahydrofuran. The resulting reaction mixture was then stirred for 3 hours at 0 to 5° C. Subsequently, 24.6 g of an aqueous 50% sodium hydroxide solution and 40 ml of methanol were added to the reaction mixture. The resulting reaction mixture was stirred for 3 hours at 60° C. After the reaction mixture was allowed to cool to room temperature, 150 ml of toluene and 100 ml of ice water were then poured into the reaction mixture to separate the reaction mixture into an aqueous layer and an organic layer. After the aqueous layer was extracted therefrom, 100 ml of a 20% hydrochloric acid solution was added the aqueous layer. The resulting aqueous layer was then extracted twice with 300 ml of toluene. After the organic layers therefrom were combined, the resulting mixture was dried with anhydrous magnesium sulfate and concentrated under reduced pressure to provide 35 g of 2,2-dimethyl-3-(1-butenyl)cyclopropanecarboxylic acid. In the isolated 2,2-dimethyl-3-(1-butenyl)cyclopropanecarboxylic acid, the molar ratio of the (Z) isomer thereof at the 1-butenyl group to the (E) isomer thereof at the 1-butenyl group was 8:1.

Fifty grams (50 g) of 2,2-dimethyl-3-(1-butenyl)cyclopropanecarboxylic acid, 350 ml of hexane and 0.6 g of N,N-dimethylformamide were mixed together. At 50° C., 39 g of thionyl chloride was eye-dropped thereto over 30 minutes. Subsequently, the reaction mixture was stirred for 1 hour at 50° C. The reaction mixture was then concentrated under reduced pressure to provide 48 g of 2,2-dimethyl-3-(1-butenyl)cyclopropane carboxylic chloride.

The Formulation Examples are provided below. The Formulation Examples 1 to 16 set forth examples of formulating the ester compounds encompassed by formula (1). In Formulation Examples 1 to 16, "parts" means parts by weight, wherein the parts by weight are based on the total weight of the provided formulation.

Formulation Example 1

After 20 parts of the present invention compounds 1 to 3 are dissolved, respectively, in 65 parts of xylene, 15 parts of Sorpol 3005X (trademark of Toho Chemical Company) are added to each of the solutions. The resulting mixtures are stirred to produce emulsifiable concentrates.

Formulation Example 2

After 5 parts of Sorpol3005X are added, respectively, to 40 parts of the present invention compounds 1 to 3, the resulting mixtures were mixed well. Subsequently, 32 parts of CARPLEX#80 (synthetic hydrated silica, trademark of Shionogi Pharmaceutical Company) and 23 parts of a 300 mesh diatomaceous earth were added to each of the mixtures. The resulting mixtures were then mixed in juice mixer to provide wettable powders.

Formulation Example 3

One and a half (1.5) parts of the present invention compounds 1 to 3 are mixed, respectively, with 98.5 parts of AGSORBLVM-MS24/48 (OIL DRI Company, sintered product of montmorillonite, a granular carrier having a granular diameter of 24 to 48 mesh). After producing granules with a granulator, the granules are air dried to provide 1.5% granules.

Formulation Example 4

Ten (10) parts of Compounds 1 to 3 are mixed, respectively, with mixtures containing 10 parts of phenylxylylethane and 0.5 parts of Sumidur L-75 (tolylenediisocyanate provided by Sumitomo Bayer Urethane Co., Ltd.). Subsequently, 0.5 parts of each of the mixtures are added, respectively, to 20 parts of a 10% aqueous solution of gum arabic. The mixtures are mixed with a homogenizer to produce an emulsion in which the mean droplet diameter therein is 20 $\mu$m. Each of the emulsions are further mixed with 2 parts of ethylene glycol and are stirred for 24 hours at 60° C. to produce microcapsule slurries.

Thickening solutions are prepared by dispersing 0.2 parts of xanthan gum and 1.0 part Beagum R (aluminum magnesium silicate; trademark of Sanyo Chemical Co., Ltd.) in 56.3 parts of ion-exchanged water.

Forty two and five-tenths (42.5) parts of each of the microcapsule slurries are mixed with 57.5 parts of the thickening agent to provide microcapsules.

Formulation Example 5

After mixing, respectively, 10 parts of the present invention compounds 1 to 3 with 10 parts of phenylxylylethane, each of the mixtures is added to 20 parts of an aqueous 10% polyethylene glycol solution. The mixtures are mixed with a homogenizer to produce emulsions in which the mean droplet diameter therein is 3 $\mu$m.

Thickening solutions are prepared by dispersing 0.2 parts of xanthan gum and 1.0 part Beagum R (aluminum magnesium silicate; trademark of Sanyo Chemical Co., Ltd.) in 56.3 parts of ion-exchanged water.

Flowables are then produced by mixing, respectively, 40 parts of the emulsion with 60 parts of the thickening solution.

Formulation Example 6

After 5 parts of the present invention compounds 1 to 3 are mixed, respectively, with 5 parts of CARPLEX#80 (synthetic hydrated silica, trademark of Shionogi Pharmaceutical Company), 0.3 parts of PAP (mono, diisopropylphosphate mixture) and 91.7 parts are added to each of the mixtures. The resulting mixture is mixed in a juice mixture to produce dusts.

Formulation Example 7

One (1) part of the present invention compounds 1 to 3 is dissolved, respectively, in 10 parts of dichloromethane. Each of the resulting mixtures are mixed with 89.9 parts of deodorized kerosene to produce oily formulations.

Formulation Example 8

One (1) part of the present invention compounds 1 to 3 is mixed, respectively, with a mixture containing 5 parts of dichloromethane and 34 parts of deodorized kerosene. The resulting mixtures are packed into aerosol vessels. After valves are attached to the aerosol vessels, 60 parts of a propellant (liquid petroleum gas) are packed into each of the aerosol vessels through the valve attached thereto to provide oil-based aerosols.

Formulation Example 9

Six-tenths (0.6) parts of the present invention compounds 1 to 3 are mixed and dissolved, respectively, in mixtures containing 5 parts of xylene, 3.4 parts of deodorized kerosene and 1 part by weight of an emulsion [Atmos 300 (a registered trade name, Atlas Chemical Corp.)]. The resulting mixtures and 50 parts of water are packed, respectively, into aerosol vessels. After valves are attached to the aerosol vessels, 40 parts of a propellant (liquid petroleum gas) are packed into each of the aerosol vessels through the valves attached thereto to provide water-based aerosols.

Formulation Example 10

A mosquito-coil component is produced by uniformly mixing Tabu powder, Pyrethrum marc and wood powder at a 4:3:3 weight ratio. After 0.3 g of the present invention compounds 1 to 3 are uniformly mixed, respectively, with 99.7 g of the mosquito-coil component, 100 ml of water is added to each of the mixtures. Mosquito coils are then produced by sufficiently kneading the mixtures, forming the mixtures into coils and drying each of the coils.

Formulation Example 11

Mosquito-mat components are produced by compacting a fibril mixture containing cotton linter and pulp into plates having the dimensions of 2.5 cm×1.5 cm with a thickness of 0.3 cm. Eight-tenths grams (0.8 g) of each of the present invention compounds 1 to 3 and 0.4 g of piperronylbutoxide are dissolved in acetone to amount to 10 ml. Five-tenths milliliters (0.5 ml) of each of the acetone solutions are uniformly impregnated onto the mosquito-mat components to provide mosquito-mats for electric heater.

Formulation Example 12

Three (3) parts of the present invention compounds 1 to 3 are dissolved, respectively, in 97 parts of deodorized kerosene and are transferred to vinyl chloride containers. A heat-tolerant wick is then added to each of the vinyl chloride containers to provide liquids for electric heaters. The heat-tolerant wick is produced by shaping an inorganic powder with a binder and sintering the inorganic powder.

Formulation Example 13

One hundred micrograms (100 $\mu$g) of each of the present invention compounds are dissolved in an appropriate amount of acetone. The resulting acetone solutions are impregnated onto porous ceramic plates having the dimensions of 4.0 cm×4.0 cm with a thickness of 1.2 cm to provide heating fumigants.

Formulation Example 14

One hundred micrograms (100 $\mu$g) of each of the present invention compounds are dissolved in an appropriate amount of acetone. The resulting acetone solutions are uniformly spread onto a filter papers having the dimensions of 2 cm×2 cm with a thickness of 0.3 cm to provide room temperature volatizing formulations.

Next, the test examples are described to demonstrate that at least the present invention compound 1 is effective as an active ingredient of a pesticidal composition.

Test Example 1

A 0.025% oily formulation was produced by dissolving 0.025 parts of the present invention compound 1 in 10 parts of dichloromethane and by mixing the resulting mixture with 89.975 parts of deodorized kerosene.

Adult houseflies (5 of each male and female) were released in a cubic chamber having a side length of 70 cm. Seven-tenths milliliters (0.7 ml) of the 0.025% oily formulation was then sprayed into the chamber from a side window of the chamber, utilizing a spray gun set to a pressure of $8.8\times10^4$ Pa. The number of knockdowned houseflies was counted periodically over 10 minutes. The time utilized to knockdown half of the tested houseflies (KT50) was determined from the number of knockdowned houseflies. The KT50 was 2.3 minutes.

The results are shown in Table 1 below.

TABLE 1

| Test compound | Concentration of oily formulation | KT50 (minutes) |
|---|---|---|
| Present invention compound 1 | 0.025 | 2.3 |

Test Example 2

A 0.1% oily formulation was produced by dissolving 0.1 part of the present invention compound 1 in 10 parts of dichloromethane and by mixing the resulting mixture with 89.9 parts of deodorized kerosene.

Ten (10) adult houseflies (5 of each male and female) were placed in a 650 ml plastic cup. The opening of the plastic cup was covered with a nylon mesh to confine the houseflies to the plastic cup. The plastic cup was placed on top of a metal screen placed in a metal chamber having the dimensions 46 cm×46 cm×70 cm. Five-tenths milliliters (0.5 ml) of the 0.01% oily formulation was then sprayed from about 30 cm above the top area of the plastic cup, utilizing a spray gun set to a pressure of $8.8\times10^4$ Pa. The number of knockdowned houseflies were counted 10 seconds thereafter. The knockdown rate was determined from the number of knockdowned houseflies achieved. The knockdown rate was 95%.

The results are shown in Table 2 below.

TABLE 2

| Test compound | Concentration of oily formulation | Knockdown rate (%) |
|---|---|---|
| Present invention compound 1 | 0.1 | 95 |

Test Example 3

Three (3) 0.00625% oily formulations were produced with the following pesticidal compounds:

(a) 2,5-dioxo-3-(2-propynyl)imidazolidin-1-ylmethyl (1R)-trans-2,2-dimethyl-3-((Z)1-propenyl)cyclopropanecarboxylate, (b) 2,5-dioxo-3-(2-propynyl)imidazolidin-1-ylmethyl (1R)-cis-2,2-dimethyl-3-((Z)1-propenyl)cyclopropanecarboxylate, and (c) the compound encompassed by formula (A) (a mixture of cis and trans isomers).

In the compound encompassed by formula (A), the weight ratio of trans isomers thereof to the cis isomers thereof is 8:2. The 0.00625% oily formulations were produced by dissolving, respectively, 0.00625 parts of the above pesticidal compounds in 10 parts of dichloromethane and by mixing each of the resulting mixture with 89.99375 parts of deodorized kerosene.

Ten (10) adult female common mosquitoes were released in each of the cubic chambers having a side length of 70 cm. Seven-tenths milliliters (0.7 ml) of the 0.00625% oily formulations were then sprayed, respectively, into each of the chambers from the side windows of the chambers, utilizing spray guns set to a pressure of $8.8\times10^4$ Pa. The numbers of knockdowned common mosquitoes were counted periodically over 10 minutes. The times utilized to knockdown half of the tested common mosquitoes (KT50) were determined from the number of knockdowned common mosquitoes. The results are shown below in Table 3.

TABLE 3

| Test Compounds | isomeric configuration | Concentration of oily formulation | KT50 (minutes) |
|---|---|---|---|
| Compound a* | 1R-trans-Z | 0.00625 | 0.99 |
| Compound b** | 1R-cis-Z | 0.00625 | 1.4 |
| Compound c*** | 1R-(cis, trans) | 0.00625 | 2.9 |

*Compound a above refers to 2,5-dioxo-3-(2-propynyl)imidazolidin-1-ylmethyl (1R)-trans-2,2-dimethyl-3-((Z)1-propenyl)cyclopropanecarboxylate
**Compound b above refers to 2,5-dioxo-3-(2-propynyl)imidazolidin-1-ylmethyl (1R)-cis-2,2-dimethyl-3-((Z)1-propenyl)cyclopropanecarboxylate
***Compound c refers to the compound encompassed by formula (A) (cis and trans isomers)

The above results achieved from Test Examples 1 to 3 evidence that the ester compounds encompassed by formula (1) provide an excellent pesticidal effect when utilized on pests.

What is claimed is:

1. An ester compound encompassed by formula (1):

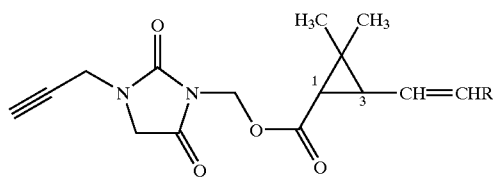

wherein, R represents a methyl group.

2. The ester compound according to claim 1, wherein in formula (1), the substituent at the 1 position of the cyclopropane ring is in a trans configuration with the substituent at the 3 position of the cyclopropane ring.

3. The ester compound according to claim 1, wherein in formula (1), the substituent at the 1 position of the cyclopropane ring is in a cis configuration with the substituent at the 3 position of the cyclopropane ring.

4. The ester compound according to claim 1, wherein in formula (1) the relative configuration of the C=C double bond at the 3 position of the cyclopropane ring moiety is a Z configuration.

5. The ester compound according to claim 1, wherein in formula (1) the absolute configuration at the 1 position of the cyclopropane ring is a R configuration.

6. A pesticidal composition comprising a carrier and an ester compound encompassed by formula (1):

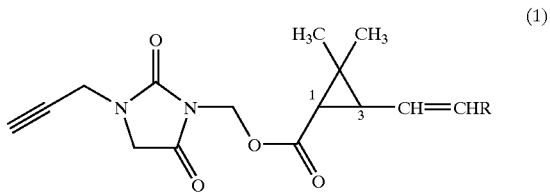

wherein, R represents a methyl group.

7. A method of controlling a pest, comprising applying to at least one location selected from the pest and a habitat of the pest, a pesticidally effective amount of an ester compound encompassed by formula (1):

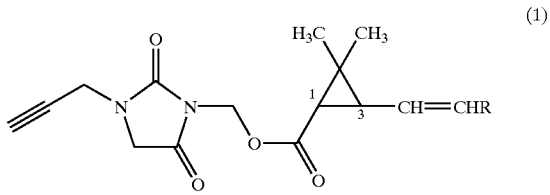

wherein, R represents a methyl group.

* * * * *